United States Patent [19]
Yatsu et al.

[11] Patent Number: 5,563,173
[45] Date of Patent: Oct. 8, 1996

[54] ANTI-PROLIFERATIVE EFFECTS OF SODIUM BUTYRATE

[75] Inventors: Frank M. Yatsu; Kasturi Ranganna, both of Houston, Tex.

[73] Assignee: Research Development Foundation, Carson City, Nev.

[21] Appl. No.: 362,829

[22] Filed: Dec. 22, 1994

[51] Int. Cl.[6] .................................................. A61K 31/19
[52] U.S. Cl. ........................................................ 514/557
[58] Field of Search .............................................. 514/557

[56] References Cited

PUBLICATIONS

Knudsen, *Biological Abstracts*, vol. 80, No. 12, Abstract 102425, 1985.
Dexter et al., *Chemical Abstracts*, vol. 94, No. 23, Abstract 186197p, 1981, p. 109.

*Primary Examiner*—Marianne M. Cintins
*Assistant Examiner*—William R.A. Jarvis
*Attorney, Agent, or Firm*—Benjamin Aaron Adler

[57] ABSTRACT

The present invention provides a method of inhibiting the proliferation of smooth muscle cells comprising the step of contacting said cells with a pharmacologically effective amount of sodium butyrate.

2 Claims, 7 Drawing Sheets

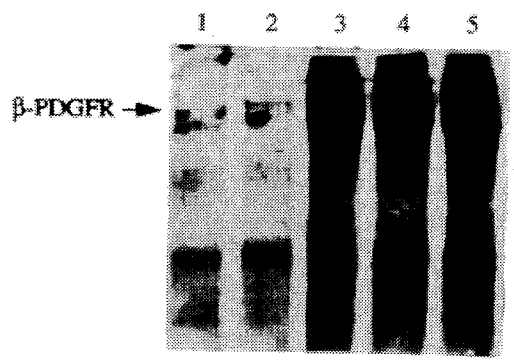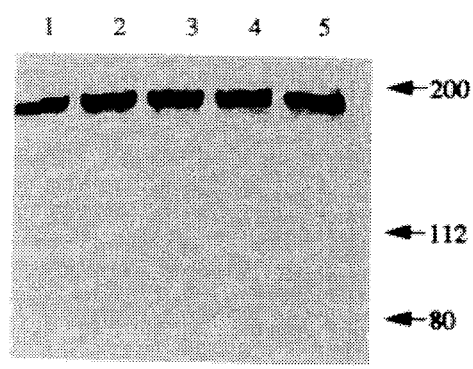
FIGURE 2A                    FIGURE 2B

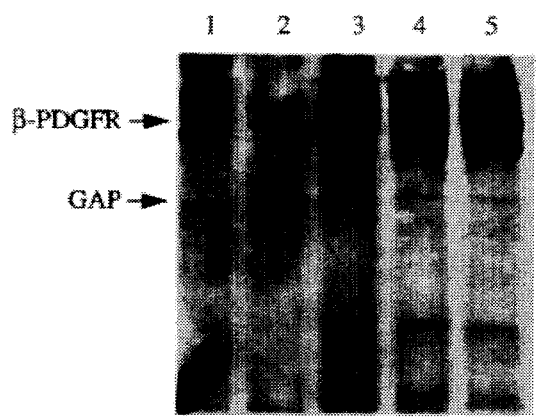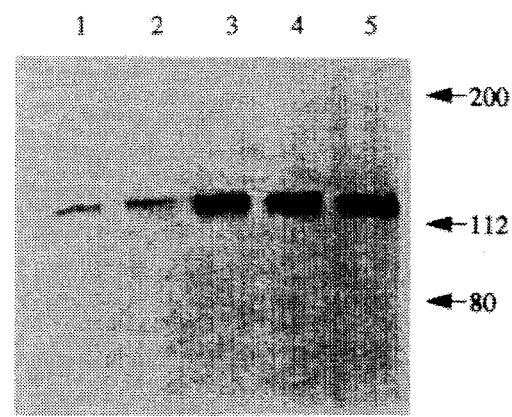
FIGURE 3A
FIGURE 3B

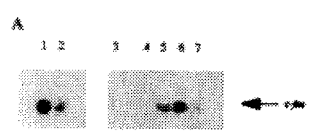
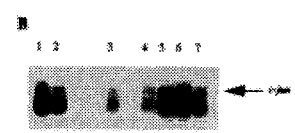
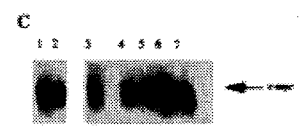
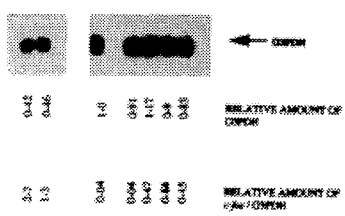
FIG. 7A  FIG. 7B  FIG. 7C

5,563,173

ANTI-PROLIFERATIVE EFFECTS OF SODIUM BUTYRATE

BACKGROUND OF THE INVENTION

1. Field of the Invention

The present invention relates generally to the fields of neurology and protein chemistry. More specifically, the present invention relates to a novel anti-proliferative effects of sodium butyrate.

2. Description of the Related Art

Atherosclerotic plaque development involves several synchronized events such as adhesion, migration, proliferation and transformation of cells and these events are mediated by growth factors and cytokines. Recently, attention has been focused on platelet-derived growth factor (PDGF) in the etiology of atherosclerosis because of its mitogenic, chemotactic, and vasoconstrictor effects on vascular smooth muscle cells (VSMC). In view of the fact that vascular smooth muscle cell proliferation contributes to hypertension, atherosclerosis and restenosis after angioplasty, development of new pharmaceutical agents to inhibit vascular smooth muscle cell proliferation is highly desirable.

Sodium butyrate, a natural bacterial fermentation product produced in mammalian colon has been shown to have a potent anti-proliferative effect on several cancer cells. In addition to its antineoplastic activity, sodium butyrate induces changes in cellular morphology, alters the expression of cellular genes, modulates hormone action and hormone receptors as well as growth factor receptors. Sodium butyrate has also been shown to inhibit the high fat diet-induced mammary tumorigenesis. Additionally, sodium butyrate has been used in preliminary clinical trails to treat certain acute leukemias and stable butyrate derivatives are developed with a view to use these compounds to treat mammary carcinoma.

The prior art is deficient in the lack of effective means of inhibiting the proliferation of vascular smooth muscle cells and retarding the atherosclerotic process involved in cerebrovascular disease. The present invention fulfills this longstanding need and desire in the art.

SUMMARY OF THE INVENTION

In one embodiment of the present invention, there is provided a method of inhibiting the proliferation of smooth muscle cells comprising the step of contacting said cells with a pharmacologically effective amount of sodium butyrate.

In another embodiment of the present invention, there is provided a pharmaceutical composition, comprising pharmacologically effective amount of sodium butyrate and a pharmaceutically acceptable carrier.

In yet another embodiment of the present invention, there is provided a method of inhibiting the formation of atherosclerotic plaques in a human comprising the step of administering to said human a pharmacologically effective amount of sodium butyrate.

In still yet another embodiment of the present invention, there is provided a method of inhibiting the formation of cerebrovascular disease in a human comprising the step of administering to said human a pharmacologically effective amount of sodium butyrate.

Other and further aspects, features, and advantages of the present invention will be apparent from the following description of the presently preferred embodiments of the invention given for the purpose of disclosure.

DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows the influence of sodium butyrate on platelet derived growth factor (PDGF)-BB-induced protein tyrosine phosphorylation. Quiescent smooth muscle cells in serum-free DMEM are exposed for 5 minutes with no addition (Lane 1), 5 mM sodium butyrate (Lane 2), preincubation in 5 mM sodium butyrate for 30 minutes and then with 5 mM sodium butyrate plus 50 ng/ml PDGF-BB (Lane 3), 50 ng/ml PDGF-BB (Lane 4) or 5 mM sodium butyrate plus 50 ng/ml PDGF-BB (Lane 5) at 37° C. After incubation, cells were lysed. Equal amounts of proteins were used for western blotting and immunoprecipitation with anti-P-tyr antibody. Whole-cell proteins and immunoprecipitates are analyzed by electrophoresis on 7.5% SDS-polyacrylamide gels, transferred to PVDF membrane and immunobloted with appropriate antibody. Immunoreactivity is detected by ECL.

FIG. 2 shows the effect of sodium butyrate on PDGF-BB-activated $\beta$-PDGFR autophosphorylation and its association with tyrosine phosphorylated proteins. Density-arrested cells were treated with similar additives as described in the description to FIG. 1 for 5 minutes at 37° C. Cells lysates were prepared and processed for immunoprecipitation and immunobloting. Similar amounts of cell lysates are used for immunoprecipitation with anti-$\beta$-PDGFR antibody. FIG. 2A shows the anti-P-tyr immunoblot of anti-$\beta$-PDGFR immunoprecipitates. FIG. 2B shows the anti-$\beta$-PDGFR immunoblot of anti-$\beta$-PDGFR immunoprecipitates.

FIG. 3 shows the effect of sodium butyrate on PDGF-BB-stimulated tyrosine phosphorylation of GTPase activating protein (GAP) and its association with $\beta$-PDGFR. Quiescent smooth muscle cells were incubated in serum-free DMEM with similar additions as described in the description to FIG. 1. Equal amounts of cell lysates were immunoprecipitated with anti-GAP and processed for immunobloting. FIG. 3A shows the anti-P-tyr immunoblot of anti-GAP immunoprecipitates. FIG. 3B shows the anti-GAP immunoblot of anti-GAP immunoprecipitates.

FIG. 4 shows the influence of sodium butyrate on PDGF-BB-provoked tyrosine phosphorylation of phospholipase C$\gamma$(PLC$\gamma$) and co-precipitation of $\beta$-PDGFR with PLC$\gamma$. Quiescent smooth muscle cells were treated as described above for 5 minutes at 37° C. Equal amounts of cell lysates are immunoprecipitated with anti-PLC$\gamma$ and processed for immunobloting.

FIG. 6 shows the sodium butyrate effect on PDGF-BB-induced and uninduced mitgen activated protein kinase (mitogen activated protein-kinase) activity. Density arrested smooth muscle cells were exposed to treatments as described above for 5 minutes at 37° C. Cell lysates were prepared and equal amounts of cell lysates were used for immunoprecipitation of mitogen activated protein-Kinase. Mitogen activated protein Kinase activities in the immunocomplexes were measured by incubating with MBP in the presence of [$\gamma$–$^{32}$P] ATP. Proteins were separated by SDS-PAGE on 12% polyacrylamide gels and autoradiographed. The phosphorylated MBP bands were excised and incorporated radioactivities are measured.

FIG. 7 shows the influence of sodium butyrate on serum and PDGF-BB-induced transcription of c-fos, c-jun and c-myc. Effect of sodium butyrate on serum and PDGF-BB-induced transcription of c-fos (A), c-jun (B) and c-myc (C) are assessed at the time of their maximal transcription (c-fos, 30 minutes; c-jun and c-myc, 60 minutes). Serum-deprived smooth muscle cells in serum-free DMEM were incubated with no addition (Lane 3), 10% fetal calf serum (Lane 10% fetal calf serum plus 5 mM sodium butyrate (Lane 2), 5 mM sodium butyrate (Lane 4), preincubation in 5 mM sodium butyrate for 30 minutes and subsequent incubation in 5 mM sodium butyrate plus 50 ng/ml PDGF-BB (Lane 5), 50 ng/ml PDGF-BB (Lane 6) or 50 ng/ml PDGF-BB plus 5 mM sodium butyrate (Lane 7) for 30 minutes or 60 minutes. After required time of incubation, total RNA are isolated and the levels of c-fos, c-jun and c-myc transcripts are measured. The RNA blots were probed with G3PDH probe to normalize the quantity of RNA loaded on to each lane.

DETAILED DESCRIPTION OF THE INVENTION

Figure 1A:
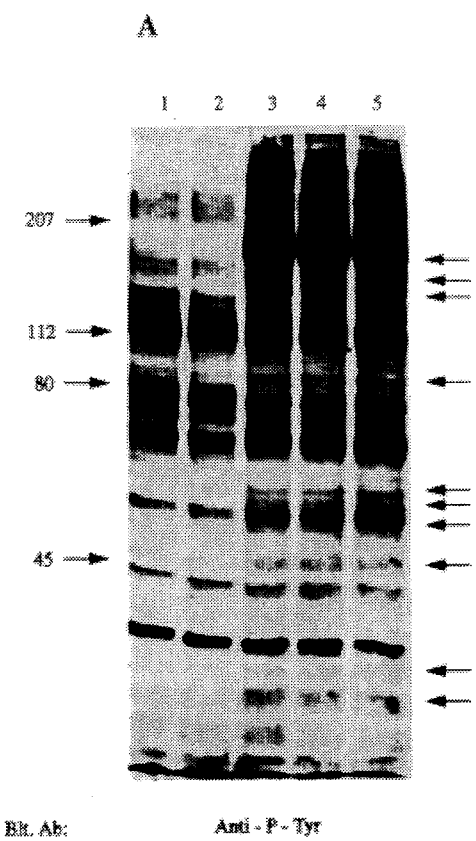
FIG. 1A shows the Anti-P-tyr immunoblot of whole-cell proteins.

The present invention is directed to a method of inhibiting the proliferation of smooth muscle cells comprising the step of contacting said cells with a pharmacologically effective amount of sodium butyrate. In this method of the present invention, the amount of sodium butyrate desirable to produce an anti-proliferative effect in smooth muscle cells is from about 0.5 mM to about 5 mM.

The present invention also provides a pharmaceutical composition, comprising pharmacologically effective amount of sodium butyrate and a pharmaceutically acceptable carrier.

The present invention is also directed to a method of inhibiting the formation of athersclerotic plaques in a human comprising the step of administering to said human a pharmacologically effective amount of the composition of claim 3.

The present invention is also directed to a method of inhibiting the formation of cerebrovascular disease in a human comprising the step of administering to said human a pharmacologically effective amount of the composition of claim 3. To produce this effect, the sodium butyrate composition is administered in a dose of from about 100 mg/kg to about 1000 mg/kg.

The following examples are given for the purpose of illustrating various embodiments of the invention and are not meant to limit the present invention in any fashion.

EXAMPLE 1

Materials

Recombinant platelet derived growth factor (PDGF)-AA, (PDGF)-AB and (PDGF)-BB were from Gibco BRL Life Technologies. Sodium butyrate was from Fluka. Anti-phosphotyrorine, anti- βPDGF-receptor, anti-GTPase activated protein and anti-PLC-γ were purchased from Upstate Biotechnology Incorporated. Anti-mitogen activated protein-Kinase, anti-RafI and protein A/G plus-agarose conjugate were from Santa Cruz Biotechnology. [Methyl–$^3$H]- thymidine, Myo-[2–$^3$H] inositol and [$\gamma$–$^{32}$P]-ATP Amersham Corporation.

EXAMPLE 2

Cell Culture

A7r5 rat aortic smooth muscle cells were obtained from American Type Culture Collection (Rockville, Md). These cells were grown in Dulbecco's Modified Eagle's medium (DMEM) fortified with 10% fetal calf serum, 50 units/ml penicillin and 50 μg/ml streptomycin. Cells were seeded into 25 cm$^2$ flask for the [$^3$H]- thymidine and myo [$^3$H]-inositol incorporation studies. For other studies cells were plated in 150 mm culture dishes. A7r5 cells were grown to 90% confluency at 37° C. in a humidified atmosphere of 5% CO$_{02}$. Culture media were changed every other day. Experiments were performed using 90% confluent cells. Quiescent cells were obtained by incubating 90% confluent cells either in 0.1% serum containing medium for 48 hours or in serum-free medium for 24 hours. For DNA synthesis measurements 10 ng/ml PDGF-AA, -AB or -BB were used. Concentration of PDGF-BB used in inositol phosphate production studies was 30 ng/ml. In protein phosphorylation, protein association, in vitro kinase assays and gene transcription experiments, 50 ng/ml PDGF-BB was used. A concentration of sodium butyrate was 5 mM unless otherwise mentioned.

EXAMPLE 3

Measurements of DNA Synthesis

Quiescent cells were stimulated with PDGF in a serum-free medium containing 1 μCi/ml [$^3$H]-thymidine in the presence or absence of sodium butyrate. After 24 hours of incubation, the cells were washed three times with phosphate buffered saline (PBS) and fixed in 2 ml of 5% ice-cold trichloroacetic acid (TCA) for 1 hour at 4° C. Fixed cells were washed three times with 5% ice-cold TCA and dissolved in 0.2 N NaOH/0.1% SDS. Amount of radioactivity incorporated was measured.

EXAMPLE 4

Phosphoinositide Assay

Quiescent cells, prelabeled with myo-[$^3$H] inositol (4 μCi/ml) for 48 hours were incubated in PBS containing 20 mM lithium chloride for 10 minutes. After 10 minutes, phosphoinositide assay was initiated by the addition of test compound and terminated after 1 minute by adding 2 ml of 5% TCA. Trichloracetic acid supernatants, collected by centrifugation were extracted three times with ether and neutralized before separating inositol phosphates on anion exchange resin (AG 1-x48; 200–400 mesh; Formate form). Inositol monophosphate (IP), inositol biphosphate (IP$_2$)and inositol triphosphates ($IP_3$) were separated according to the protocol described by Berridge et. al., *Biochem. J.* 212, 473–482 (1983). Radioactivity in each of these inositol phosphates was determined by liquid scintillation counting.

EXAMPLE 5

Immunoblots

Cells were grown in 150 mm culture plates and washed with ice-cold PBS three times and lysed in 1 ml of RIPA buffer (20 mM Tris, pH. 7.4, 137 mM NaCl, 10% glycerol, 0.1% SDS, 0.5% sodium deoxycholate, 1% Triton X-100, 2 mM EDTA, 1 mM PMSF, 20 µM leupeptin and 1 mM Sodium orthovanadate) by gently rocking for 20 minutes at 4° C. Lysates were then sheared with syringe and needle and clarified by centrifugation. The clear lysates were normalized for total cellular protein and equal amount of protein from each lysate was fractionated on SDS-polyacrylamide gel and transferred to immobilon PVDF membrane and blocked for 1 hour in blocking buffer containing 5% non-fat dry milk and 0.1% Tween 20 in Tris-buffered saline (TBS). Blots were washed three times with Tris-buffered saline containing 0.1% Tween 20 (TBST) and probed with appropriate primary antibody for 1 hour in TBS. Blots were washed three times with TBST and then incubated with appropriate second antibody conjugated to horseradish peroxidase. Immunoreactive proteins were identified using ECL chemiluminescence detection kit from Amersham corporation.

EXAMPLE 6

Immunoprecipitations

Cell lysates were prepared as described above using RIPA buffer. Equal amount of proteins were incubated with βPDGF-receptor, ras GTPase activated protein, PLC-γ or P-Tyr antibody and protein A/G plus agarose-conjugates for about 12 hours at 4° C. Immunoprecipitated complexes were collected by centrifugation, washed once with RIPA buffer, twice with 0.5 M LiCl in 0.1 M Tris, pH.7.4 and once with 10 mM Tris, pH.7.4. Immunoprecipitated proteins were eluted with SDS-PAGE buffer and separated on 7.5% gels. Separated proteins were transferred to immobilon PVDF membrane and used for immunobloting with suitable antibodies.

EXAMPLE 7

Mitogen-Activated Protein Kinase Assay

Cell lysates were prepared by using nonionic detergent buffer containing 1% Triton X-100, 20 mM Tris, ph-8.0, 137 mM NaCl 10% glycerol, 2 mM EDTA, 1 mM PMSF, 20 µM leupeptin an 1 mM sodium orthovanadate as described above. Similar amounts of proteins were incubated with polyclonal mitogen activated protein-Kinase antibody for 2 hours at 4° C. and protein A/G plus agarose-conjugate is added for the last 30 minutes. Immunocomplexes were collected, washed twice with nonionic detergent buffer followed by one wash in TBS supplemented with 1 mM sodium orthovanadate and 5 mM benzamidine. Mitogen activated protein-kinase activity was measured by incubating the immunopreciptitation with 40 µl of kinase reaction mix (30 mM Tris, pH.8.0) 10 mM $MgCl_2$, 20 µM ATP, 1 mM DTT, 5 mM benzamidine, 10 µCi of [γ-$^{32}$P] ATP and 6 µg of myelin basic protein and incubating for 30 minutes at 37° C. The reaction was terminated by adding 20 µl of 4x SDS-PAGE buffer. Reaction products were analyzed by SDS-PAGE on a 12% gel followed by autoradiography. Phosphorylated MBP was excised from the gel and the radioactivity was measured.

EXAMPLE 8

RNA Isolation and Northern Analysis

Quiescent smooth muscle cells grown in 150 mm culture dishes were exposed to different treatments for times indicated in the relevant result section. Total RNA was isolated using TRI reagent method (Molecular Research Center, Cincinnati, OH). For Northern analysis, 15 µg of total RNA was denatured in sample loading buffer containing 1 µg/ml ethidium bromide and electrophoresed through 1% agarose formaldehyde gel. RNA was transferred to S&S MaxS nytran membrane by downward alkaline transfer method using S&S Turbo Blotter transfer system. Transferred RNA was fixed to nytran membrane by UV irradiation. Random primed c-fos, c-jun and c-myc probes were used for hybridization according to the protocol of Gilbert and Church, *Proc. Natl. Acad. Sci.* 81:1991–1995 (1984). Blots were exposed to Hyperfilm-MP (Amersham Corp.) with intensifying screen at −70° C for 1–3 days.

EXAMPLE 9

Measurements of DNA synthesis

Incorporation of [$^3$H]-thymidine into DNA was used as a measure of cell proliferation. Growth arrested smooth muscle cells were exposed to PDGF-AA, -AB or -BB with or without 5 mM sodium butyrate for 24 hours in the presence of [$^3$H]-thymidine. After 24 hours, the amount of [H]-thymidine incorporated was measured. Table I shows that although PDGF is a potent mitogen for smooth muscle cells, not all three isoforms are equally potent. PDGF-AA was the least potent and PDGF-BB was the most potent of the three isoforms of PDGF. Accordingly, PDGF-AA, PDGF-AB and PDGF-BB stimulated DNA synthesis by 3-, 5- and 9- fold respectively compared to uninduced smooth muscle cells. However, in the presence of 5 mM sodium butyrate, PDGF-induced DNA synthesis is inhibited more than 80% irrespective of the isoform used. At 5 mM concentration, sodium butyrate has no significant effect on DNA synthesis compared to uninduced smooth muscle cells.

TABLE I

Inhibition of PDGF-AA, PDGF-AB and PDGF-BB stimulated rat aortic smooth muscle cell proliferation by sodium butyrate

| Addition | dpm × $10^{-3}$/flask |
| --- | --- |
| None | 559 ± 154 |
| Sodium butyrate | 650 ± 154 |
| PDGF-AA | 1759 ± 314 |
| PDGF-AA + Sodium butyrate | 677 ± 78 |
| PDGF-AA | 2882 ± 229 |
| PDGF-AB + Sodium butyrate | 445 ± 46 |
| PDGF-BB | 5168 ± 604 |
| PDGF-BB + Sodium butyrate | 645 ± 23 |

Following growth arrest in serum-free DMEM medium for 24 hours, cells were induced to proliferate in serum-free DMEM medium containing [$^3$H]-thymidine with PDGF-AA, PDGF-AB and PDGF-BB in the presence or absence of 5 mM sodium butyrate. Each value is mean ±S.D. of a minimum of four measurements and representative of three experiments.

Since PDGF BB is the most effective isoform of PDGF, it was used to demonstrate the effective concentration of sodium butyrate on PDGF-BB-induced proliferation (Table II). The effect of sodium butyrate on PDGF-BB-induced DNA synthesis was measured between the concentration of 1 µM to 10 mM. Between 1 µM and 0.5mM, sodium butyrate had no effect on PDGF-BB-induced DNA synthesis (data not shown). Between 0.5 mM and 1 mM sodium butyrate there was about 20% inhibition of PDGF-BB-induced DNA synthesis. Higher than 1 mM concentration of sodium butyrate exhibit significant inhibition of PDGF-BB-induced DNA synthesis. Between 5 mM and 8 mM, there was complete inhibition of PDGF -BB-induced DNA synthesis. However, at these concentrations the smooth muscle cells appeared phenotypically normal although there was a decrease in PDGF-induced cellular protein content (data not shown). Since 5 mM concentration of sodium butyrate almost completely inhibited PDGF-BB-induced DNA synthesis without any visual adverse effect on smooth muscle cells, this concentration of sodium butyrate was selected to illustrate the mechanism of inhibition of PDGF-BB-induced proliferation.

TABLE II

Effect of sodium butyrate on PDGF-BB-induced proliferation of rat aortic smooth muscle cells.

| Sodium butyrate | dpm × 10⁻³/flask | |
| --- | --- | --- |
| | −PDGF-BB | +PDGF-BB |
| 0 | 1031 ± 258 | 3904 ± 184 |
| 1 mM | 1268 ± 177 | 3071 ± 370 |
| 3 mM | 1218 ± 63 | 1236 ± 151 |
| 5 mM | 1173 ± 99 | 1054 ± 29 |
| 8 mM | 882 ± 145 | 777 ± 71 |

Rat aortic smooth muscle cells are grown to 90% confluency and then rendered quiescent by incubating in serum-free DMEM medium for 24 hours. Quiescent cells are stimulated in serum-free medium containing [$^3$H]-thymidine with PDGF-BB in the presence or absence of different concentrations of sodium butyrate. Data presented are mean ±S.D. and representative of two independent experiments.

EXAMPLE 10

PDGF-BB Induced Down-Regulation of β-PDGF-receptor (β-PDGF-R)

Figure 1B:
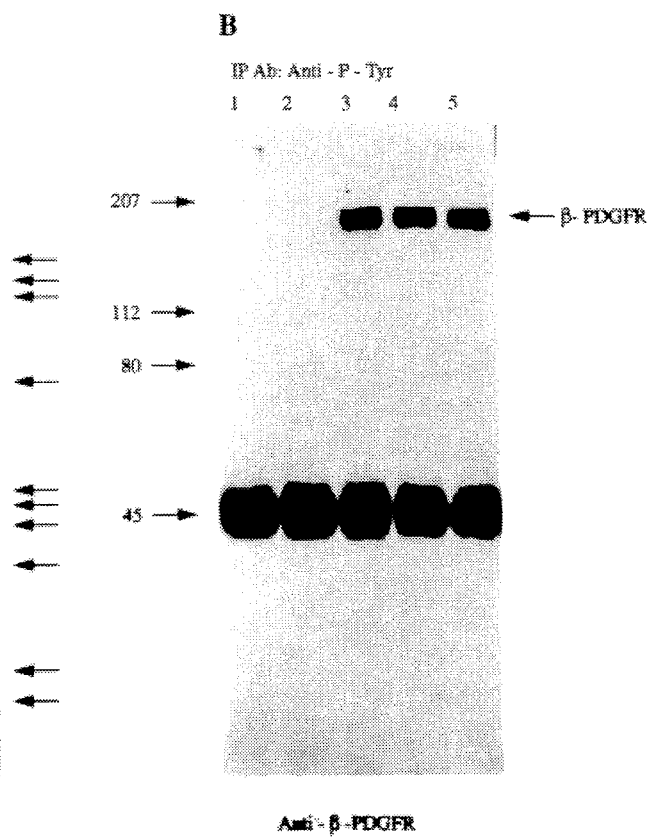
FIG. 1B shows the Anti-$\beta$-PDGFR immunoblot of anti-P-Tyr immunoprecipitates.

In view of understanding the mechanism of inhibition of PDGF-BB-induced proliferation by sodium butyrate afforded by the present invention, the influence of sodium butyrate on PDGF-BB stimulated β-PDGF-R modification was next shown because the PDGF -BB signal is transduced through the receptor into the cell. Cell lysates obtained from smooth muscle exposed to no addition, PDGF -BB, sodium butyrate and PDGF-BB plus sodium butyrate for different lengths of time were analyzed by SDS-PAGE followed by immunoblotting with anti-β-PDGF-R to study the receptor down-regulation (FIG. 1). As shown in FIG. 1A, β-PDGF-R down-regulation occured after 2 hours of incubation of smooth muscle-cells with PDGF-BB. This time-dependent, PDGF-BB-activated, down-regulation of β-PDGF-R was unaffected by sodium butyrate (FIG. 1C). Cells exposed to PDGF-BB plus sodium butyrate exhibit a similar pattern of β-PDGF-R down-regulation as PDGF-BB treated cells. On the other hand, β-PDGF-R undergo no degradation when smooth muscle cells were exposed to sodium butyrate alone (FIG. 1B) indicating sodium butyrate did not interfere with ligand-stimulated receptor down-regulation

EXAMPLE 11

PDGF-BB-Induced Protein Tyrosine Phosphorylation

Tyrosine phosphorylation of proteins has been implicated in mitogenic signal pathway. Therefore, the PDGF-BB stimulated protein phosphorylation and its response to sodium butyrate treatment was probed. Total cellular lysate as well as anti-P-tyrosine immunoprecipitates were prepared from smooth muscle cells and subject to immunoblotting with anti-P-tyrosine and anti-PDGFR, respectively (FIGS. 2A and 2B). Cells exposed to PDGF-BB or PDGF-BB plus sodium butyrate exhibit increased protein tyrosine phosphorylation. In addition there were no obvious differences in the protein tyrosine phosphorylation profile between the two treatments (FIG. 2A). Similarly, pre-treatment of cells for 30 minutes with sodium butyrate and subsequent exposure to PDGF-BB plus sodium butyrate had no effect on PDGF-BB-induced protein tyrosine phosphorylation profile (FIG. 2A). In the absence of PDGF-BB there was no increased phosphorylation of protein.

PDGF-BB-induced, β-PDGF-R autophosphorylation was also unaffected by sodium butyrate irrespective of whether the cells were exposed to sodium butyrate before PDGF-BB or together with PDGF-BB (FIG. 2B). In the absence of PDGF-BB as well as in the presence of sodium butyrate alone there is no β-PDGF-R reaction with anti-P-tyrosine antibody, indicating that sodium butyrate was not interfering with PDGF-BB-induced tyrosine phosphorylation of β-PDGF-R as well as cellular proteins.

EXAMPLE 12

Association of Signaling Molecules with Tyrosine Phosphorylated β-PDGF-R

PDGF-treatment of cells has been shown to result in PDGF-R association and tyrosine phosphorylation of signaling molecules such as PLCγ,Raf 1, ras GTPase activated protein and PI-3 kinase. To ascertain whether inhibition of PDGF-BB-induced proliferation of smooth muscle cells by sodium butyrate involves disruption of this process, β-PDGF-R immunoprecipitates were examined for the presence of PLCγ and ras GTPase activated protein. β-PDGF-R immunoprecipitation were prepared from smooth muscle cells and analyzed by immunoblotting using anti-P-tyrosine. As shown in FIG. 3A, treatment of cells with no additions or sodium butyrate alone neither induced β-PDGF-R phosphorylation nor protein association. On the other hand, PDGF-BB induced not only β-PDGF-R phosphorylation but also promoted association and phosphorylation of PLCγ, GTPase activated protein and a 74 Kd protein with β-PDGF-R (FIG. 3A). Presence of β-PDGF-R, (FIG. 3B), PLCγ and GTPase activated protein (data not shown) were confirmed by re-probing the blot with corresponding antibodies. The identity of 74 Kd phosphorylated protein was not confirmed, but presumably is Raf-1 kinase. Incubation of smooth muscle cells with PDGF-BB plus sodium butyrate or pre-incubation with sodium butyrate alone for 30 minutes and subsequent incubation with PDGF- BB plus sodium butyrate did not alter PDGF-BB-stimulated β-PDGF-R phosphorylation and its association and phosphorylation of PLCγ, GTPase activated protein and 74 Kd protein. Thus, inhibition of PDGF-BB-induced proliferation of smooth muscle cells by sodium butyrate did not involve a signal transduction pathway associated with PLCγ and ras GTPase activated protein. This was further confirmed by the analysis of ras GTPase activated protein and PLCγ immunoprecipitates.

EXAMPLE 13

Tyrosine Phosphorylation of ras GTPase Activated Protein and

Association with β-PDGF-R

Figure 4A:
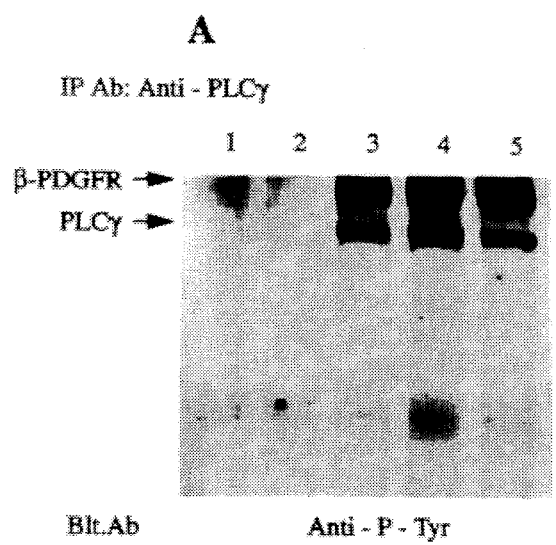
FIG. 4A shows the Anti-P-tyr immunoblot of anti-PLC$\gamma$ immunoprecipitates.
Figure 4B:
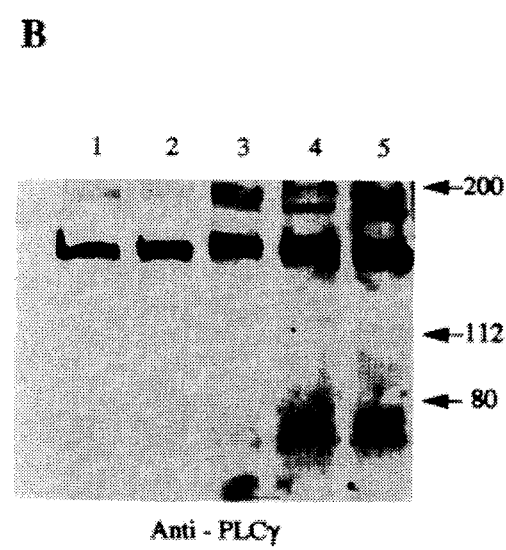
FIG. 4B shows the Anti-PLC$\gamma$ immunoblot of anti-PLC$\gamma$ immunoprecipitates.

Immunoprecipitates of ras GTPase activated protein were prepared from cell lysates and analyzed by immunobloting with anti-P-tyrosine or anti-ras GTPase activated protein (FIGS. 4A and 4B). Anti-P-tyrosine immunoblot identified β-PDGF-R, PLCγ, ras GTPase activated protein and a protein of 74 Kd in the samples that were exposed to PDGF-BB with or without sodium butyrate as well as in samples that are pretreated with sodium butyrate and then incubated in PDGF-BB plus sodium butyrate. Thus, sodium butyrate had no effect on β-PDGF-R induced protein association and phosphorylation of ras GTPase activated protein (FIG. 4A). Sodium butyrate by itself had no effect either on protein phosphorylation or on protein association. Therefore, no proteins were identified in cells that were exposed to sodium butyrate, as in, no addition treatments. When the blot was re-probed with anti-ras GTPase activated protein, ras GTPase activated protein was visible in all the treatments (FIG. 4B).

EXAMPLE 14

Phosphorylation of PLCγ and its Association with β-PDGF-R

Figure 5:
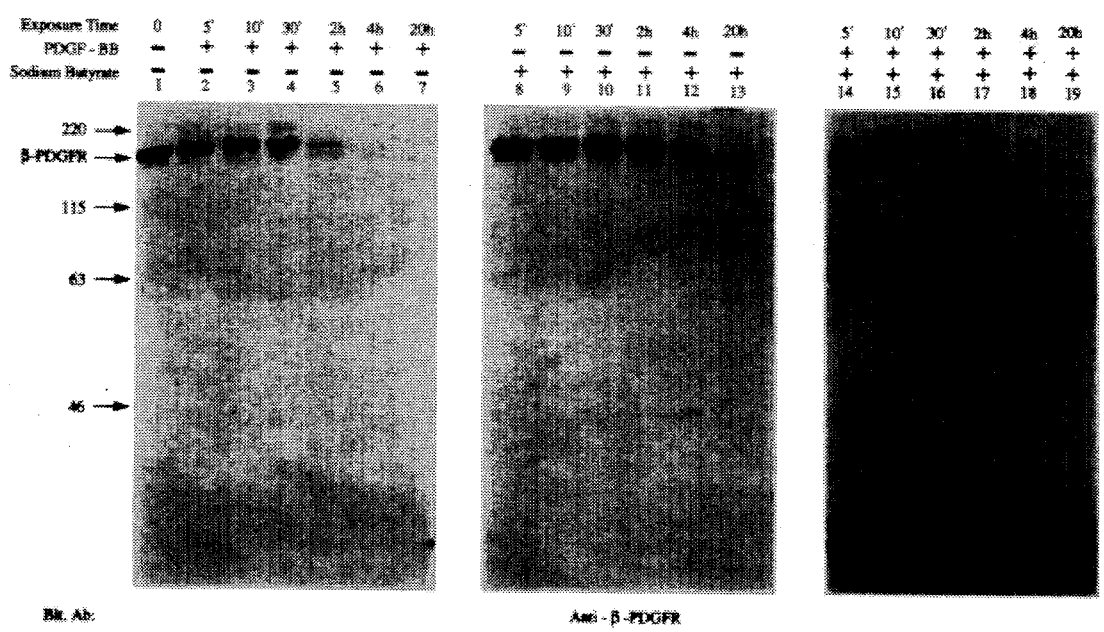
FIG. 5 shows the PDGF-BB-Induced $\beta$-PDGFR degradation. Serum-starved smooth muscle cells were incubated in serum-free DMEM containing no additions, 50 ng/ml PDGF-BB, 5 mM sodium butyrate or 50 ng/ml PDGF-BB plus 5 mM sodium butyrate for indicated periods of time. Cell lysates were prepared and equal amounts of cell lysates are subjected to polyacrylamide gel electrophoresis. After electrophoresis β-PDGFR degradation is detected by probing with anti β-PDGFR antibody.

The effect of sodium butyrate on PDGF-BB-induced phosphorylation of PLCγ and its association with activated β-PDGF-R was shown by immunoprecipitating smooth muscle cell lysate with anti-PLCγ and probing with anti-P-tyrosine or anti-PLCγ antibody (FIG. 5A and B). As expected, smooth muscle cells exhibited no phosphorylated proteins after exposure to no addition or sodium butyrate. Exposure of smooth muscle cells to PDGF-BB, activates association and phosphorylation of β-PDGF-R, PLCγ and a protein of 74Kd (FIG. 5A). The identity of β-PDGF-R (data not shown) and PLCγ (FIG. 5B) was confirmed by probing the blot with corresponding antibodies. Exposure of smooth muscle cells to PDGF-B B plus sodium butyrate or pretreatment of smooth muscle cells with sodium butyrate for 30 minutes and subsequent incubation in PDGF-BB plus sodium butyrate, has no effect on PDGF-BB-induced association and phosphorylation of β-PDGF-R and PLCγ. Thus, the mechanism of inhibition of PDGF-BB-induced proliferation by sodium butyrate was not through the signaling pathway mediated by PLCγ. Additional support was obtained by determining PDGF-BB stimulated, PLCγ-mediated $IP_3$ production. Exposure of smooth muscle cells to PDGF-BB results in an approximate 30% increase in $IP_3$ formation which is increased to 60% by incubating smooth muscle cells in the presence of PDGF-BB plus sodium butyrate (Table III). Thus, the signaling pathway that associates with PLCγ was not the target for the sodium butyrate inhibition of PDGF-BB-induced proliferation.

TABLE III

Effects of Sodium Butyrate on PDGF-BB-induced inositol phosphate production.

| | dpm × $10^{-3}$/flask | | |
|---|---|---|---|
| Addition | IP | $IP_2$ | $IP_3$ |
| None | 105 ± 10 | 11 ± 1.4 | 3.5 ± 0.7 |
| Sodium butyrate | 99 ± 14 | 10 ± 0.2 | 3.3 ± 02 |
| PDGF-BB | 110 ± 14 | 12 ± 0.9 | 4.7 ± 0.5 |
| PDGF-BB + Sodium butyrate | 117 ± 9 | 12 ± 0.5 | 5.7 ± 0.4 |

In TABLE III, rat aortic smooth muscle cells are prelabeled with [$^3$H] myoinositol for 48 hours and then exposed to PDGF-BB, sodium butyrate or sodium butyrate plus PDGF-BB for 1 minute. Inositol phosphates were separated and measured. Values are the mean ±S.D. of at least four measurements and representative of two experiments.

EXAMPLE 16

PDGF-BB-Induced Mitogen Activated Protein Kinases Activity

Figures 6A, 6B:
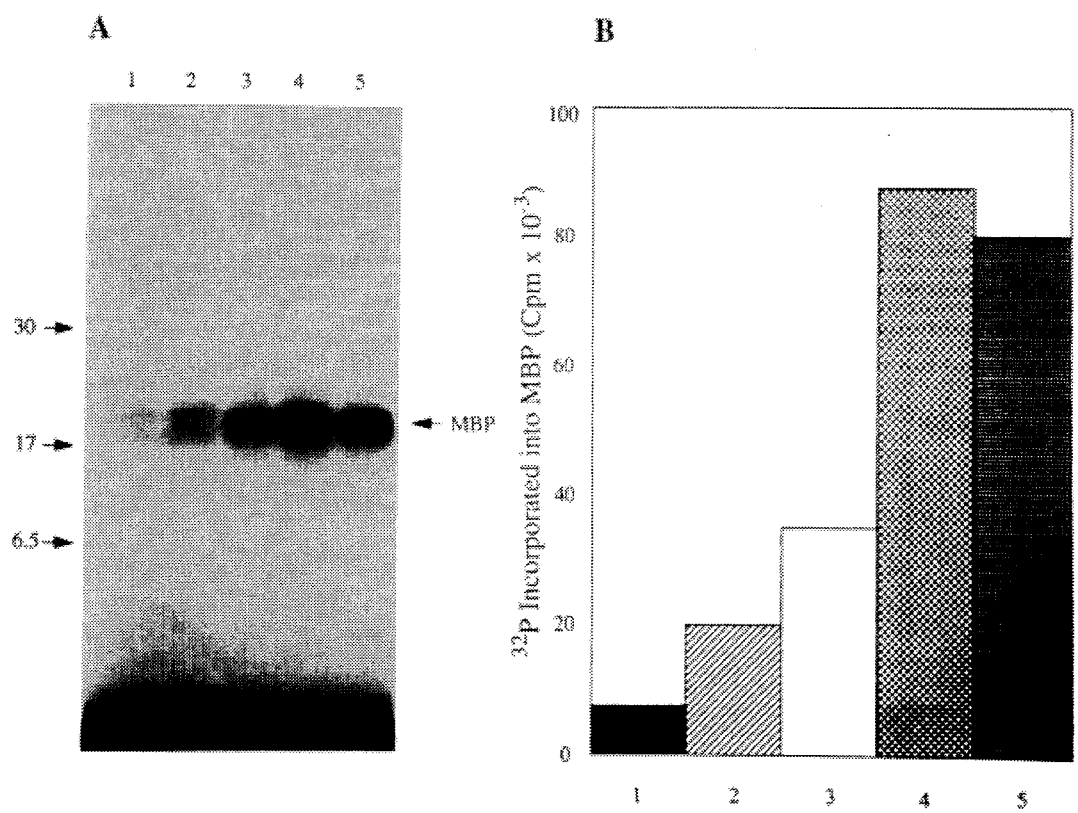
FIG. 6A shows the autoradiogram of phosphorylated MBP.
FIG. 6B shows the quantitation of MBP phosphorylation by Cerenkov counting.

Mitogen activated protein-kinases are serine and threonine kinases that are strongly activated by PDGF. The effect of sodium butyrate on PDGF-BB-induced mitogen activated protein kinase activity was measured by immunocomplex kinase assay. mitogen activated protein-kinase was immunoprecipitated from the smooth muscle cells cell lysates using an anti-mitogen activated protein-kinase antibody and the immunocomplex was subjected to in vitro kinase reaction using myelin basic protein as a substrate (FIG. 6). Surprisingly, exposure of smooth muscle cells to sodium butyrate also stimulates mitogen activated protein-kinase activity by about 2.7-fold over no addition control. Addition of PDGF-BB to smooth muscle cells stimulates mitogen activated protein-kinase activity by about 11.4-fold. This PDGF-BB stimulated mitogen activated protein-kinase activity was unaffected when smooth muscle cells were exposed to PDGF-BB plus sodium butyrate. But, preincubation of smooth muscle cells with sodium butyrate for 30 minutes and subsequent addition of PDGF-BB plus sodium butyrate resulted in a significant decrease in PDGF-BB-induced mitogen activated protein-kinase activity. There was only a 4.6-fold increase in activity over the "no addition" control suggesting that mitogen activated protein-kinase activities were differentially modified by sodium butyrate.

EXAMPLE 17

Serum and PDGF-BB-Induced Transcription of c-fos, c-jun and c-myc

Exposure of cells to serum or growth factors causes increased rapid transcription of nuclear protooncogenes. The effect of sodium butyrate on serum and PDGF-BB-induced transcription of c-fos, c-jun and c-myc was demonstrated. FIG. 7 shows that treatment of serum-starved smooth muscle cells with serum caused increased transcription of all three nuclear protooncogenes compared to the no addition control. The serum induced effect was more dramatic on c-fos and c-jun than on c-myc. Addition of sodium butyrate along with serum diminished the serum induced transcription of c-fos, c-jun and c-myc. Similar to serum, PDGF-BB also induced the transcription of all three protooncogenes. Sodium butyrate diminished the PDGF-BB stimulated transcription of c-fos, c-jun and c-myc. irrespective of whether the cells were pretreated with sodium butyrate and then exposed to sodium butyrate plus PDGF-BB or treated simultaneously with PDGF-BB plus SB. However, inhibition of c-myc transcription is more severe than inhibition of c-fos and c-jun transcription.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of inhibiting the proliferation of smooth muscle cells comprising contacting said cells with a pharmacologically effective amount of sodium butyrate.

2. The method of claim 1, wherein said amount of sodium butyrate is from about 0.5 mM to about 5 mM.

* * * * *

UNITED STATES PATENT AND TRADEMARK OFFICE
CERTIFICATE OF CORRECTION

PATENT NO. : 5,563,173
DATED : October 8, 1996
INVENTOR(S) : Frank M. Yatsu, et al It is certified that error appears in the above-identified patent and that said Letters Patent is hereby corrected as shown below:

In Column 1, line 8, "effects" should read --effect--.

In Column 1, line 33, "trails" should read --trials--.

In Column 1, lines 50-51, please insert the word --a-- between the words "comprising" and "pharmacologically".

In Column 1, lines 54-55, "athersclerotic" should read --atherosclerotic--.

In Column 2, line 25, "immunobloted" should read --immunoblotted--.

In Column 2, line 34, "Cells" should read --Cell--.

In Column 2, line 36, "immunobloting" should read --immunoblotting--.

In Column 2, lines 48-49, "immunobloting" should read --immunoblotting--.

In Column 2, line 58, "immunobloting" should read --immunoblotting--.

UNITED STATES PATENT AND TRADEMARK OFFICE
CERTIFICATE OF CORRECTION

PATENT NO. : 5,563,173
DATED : October 8, 1996
INVENTOR(S) : Frank M. Yatsu, et al It is certified that error appears in the above-identified patent and that said Letters Patent is hereby corrected as shown below:

In Column 3, line 4, "mitgen" should read --mitogen--.

In Column 3, line 9, "Kinase" should read --kinase--.

In Column 3, line 10, "Kinase" should read --kinase--.

In Column 3, line 26, please insert --1),-- between "(Lane" and "10%".

In Column 3, line 53, "athersclerotic" should read --atherosclerotic--.

In Column 4, lines 6-7 "Anti-phosphotyrorine" should read --Anti-phosphotyrosine--.

In Column 4, line 10, "Kinase" should read --kinase--.

In Column 4, line 12, please insert the words --were from-- between the words "-ATP" and "Amersham".

UNITED STATES PATENT AND TRADEMARK OFFICE
CERTIFICATE OF CORRECTION

PATENT NO. : 5,563,173
DATED : October 8, 1996
INVENTOR(S) : Frank M. Yatsu, et al

It is certified that error appears in the above-identified patent and that said Letters Patent is hereby corrected as shown below:

In Column 4, line 24, "flask" should read --flasks--.

In Column 4, line 28, "$CO_{02}$" should read --$CO_2$--.

In Column 5, lines 29-30, "corporation" should read --Corporation--.

In Column 5, line 45, "immunobloting" should read --immunoblotting--.

In Column 5, line 55, "an" should read --and--.

In Column 5, line 57, "Kinase" should read --kinase--.

In Column 5, line 64, "immunopreciptitation" should read --immunoprecipitation--.

In Column 6, line 30, "synthesis" should read --Synthesis--.

In Column 6, line 37, "[H]" should read --[$^3$H]--.

In Column 6, line 42, please insert a comma after "3-".

UNITED STATES PATENT AND TRADEMARK OFFICE
CERTIFICATE OF CORRECTION

PATENT NO. : 5,563,173
DATED : October 8, 1996
INVENTOR(S) : Frank M. Yatsu, et al

It is certified that error appears in the above-identified patent and that said Letters Patent is hereby corrected as shown below:

In Column 6, line 43, please remove the comma prior to "5-".

In Column 6, line 59, in the fifth line of TABLE I under the heading "Addition", "PDGF-AA" should read --PDGF-AB--.

In Column 7, line 12, "concentration" should read --concentrations--.

In Column 7, line 19, "concentration" should read --concentrations--.

In Column 7, line 48, "-receptor" should read -- -Receptor--.

In Column 7, line 67, "undergo" should read --underwent--.

In Column 8, line 3, please insert a period after the word "regulation".

In Column 8, line 15, "subject" should read --subjected--.

UNITED STATES PATENT AND TRADEMARK OFFICE
CERTIFICATE OF CORRECTION

PATENT NO. : 5,563,173
DATED : October 8, 1996
INVENTOR(S) : Frank M. Yatsu, et al It is certified that error appears in the above-identified patent and that said Letters Patent is hereby corrected as shown below:

In Column 8, line 49, "immunoprecipitation" should read --immunoprecipitates--.

In Column 8, line 57, please remove the comma after "β-PDGF-R".

In Column 9, lines 11-14, please remove the spaces between the heading in line 11 "Protein and" and the heading in line14 "Association with β-PDGF-R".

In Column 9, line 16, "immunobloting" should read --immunoblotting--.

In Column 9, line 44, "FIG." should read --FIGS.--.

In Column 9, line 47, please remove the comma after "PDGF-BB".

In Column 10, line 10, in the second line of TABLE III under the heading "$IP_3$", "3.3±02" should read --3.3±0.2--.

In Column 10, line 30, "mitogen" should read --Mitogen--.

UNITED STATES PATENT AND TRADEMARK OFFICE
CERTIFICATE OF CORRECTION

PATENT NO. : 5,563,173
DATED : October 8, 1996
INVENTOR(S) : Frank M. Yatsu, et al It is certified that error appears in the above-identified patent and that said Letters Patent is hereby corrected as shown below:

In Column 10, line 31, please remove the word "cells" between the words "muscle" and "cell".

In Column 11, line 3, please insert a comma after "c-myc" and delete the period prior to the word "irrespective".

In column 9, lines 10 and 11, "Activated Protein" should read --activated protein-- and line 14, "Association" should read --association--.

Signed and Sealed this

Tenth Day of November 1998

Attest:

BRUCE LEHMAN

Attesting Officer

Commissioner of Patents and Trademarks